United States Patent

[19]

Newton et al.

[11] Patent Number: 6,096,688

[45] Date of Patent: Aug. 1, 2000

[54] OXAZOLE CARBOXAMIDE HERBICIDES

[75] Inventors: Trevor Newton, Schwabenhiem; Isabel Waldeck, Heidesheim, both of Germany

[73] Assignee: American Cyanamid Company, Madison, N.J.

[21] Appl. No.: 08/995,746

[22] Filed: Dec. 22, 1997

Related U.S. Application Data

[60] Provisional application No. 60/034,420, Dec. 27, 1996.

[51] Int. Cl.$^7$ .......................... A01N 43/76; A01N 43/40; C07D 413/00; C07D 263/00
[52] U.S. Cl. ...................... 504/270; 504/251; 504/252; 504/244; 546/268.1; 546/268.4; 546/271.1; 546/274.1; 548/215; 548/235; 548/236
[58] Field of Search ...................................... 504/270, 251, 504/252; 548/235, 236; 546/268.4, 274.1, 271.1

[56] References Cited

U.S. PATENT DOCUMENTS 5,244,867   9/1993   Ditrich et al. .......................... 504/266

FOREIGN PATENT DOCUMENTS

94/27983   12/1994   WIPO .......................... C07D 277/56

OTHER PUBLICATIONS

Kashima et al., (CA 115:256626, J. Heterocycl. Chem. (1991), 28(5), 1241–4).

*Primary Examiner*—Jose' G. Dees
*Assistant Examiner*—Sabiha N. Qazi
*Attorney, Agent, or Firm*—Charles F. Costello, Jr.

[57] ABSTRACT

The novel compounds of formula I:

(I)

wherein $R^1$, $R^2$, $R^3$, $R^4$ and Ar have the meaning given in claim 1, and herbicidal compositions containing such compounds as active ingredients.

14 Claims, No Drawings

OXAZOLE CARBOXAMIDE HERBICIDES

This application claims the benefit of U.S. Provisional application Ser. No. 60/034,420, filed Dec. 27, 1996.

BACKGROUND OF THE INVENTION

This invention relates to certain novel amides of oxazole-2-carboxylic acids, to the preparation of such compounds, to herbicidal compositions containing such compounds, and to a method of combating undesired plant growth using such compounds.

U.S. Pat. No. 5,244,867 describes certain amides of 2,4-disubstituted oxazole-5-carboxylic acids and of 2,5-disubstituted oxazole-4-carboxylic acids and the herbicidal activities thereof. The compounds of this patent bear a formyl, a 4,5-dihydrooxazole or a carboxylate group in the 4- or 5-position. There is no hint to oxazoles in which the carboxamide group is attached to the 2-position of the oxazole ring.

The compounds are alleged to have herbicidal activity against various species when applied at a dosage from 0,001 to 5 kg per hectare; however, only the activity at a dosage of 1 kg per hectare has been reported.

SUMMARY OF THE INVENTION

We have now found that, surprisingly, oxazole-2-carboxamides show excellent herbicidal activity at and below dosages which are lower than the ranges disclosed in the aforementioned patents (for example at 800 g/ha), combined with good selectivity in crops.

Accordingly, the present invention provides novel compounds of the general formula I

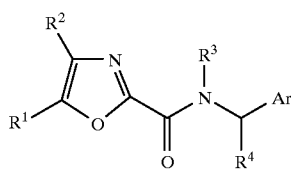

(I)

wherein
- $R^1$ and $R^2$ each independently represent a hydrogen atom or an optionally substituted alkyl, alkenyl, cycloalkyl, cycloalkenyl, aryl, heteroaryl, aralkyl or heteroaralkyl group;
- $R^3$ represents a hydrogen atom or an alkyl or acyl group;
- $R^4$ represents a hydrogen atom or an alkyl group; and
- Ar represents an optionally substituted aryl or heteroaryl group.

DETAILED DESCRIPTION

It has surprisingly been found that the novel compounds of formula I in which $R^1$ through $R^4$ and Ar have the meaning given above for formula I show excellent herbicidal activity against a broad range of weeds.

Generally, when any of the above mentioned moieties comprises an alkyl group, this alkyl group may be linear or branched and may suitably contain 1 to 10, preferably 1 to 6 carbon atoms. Examples of such groups are methyl, ethyl, n-propyl, i-propyl, n-butyl, i-butyl, s-butyl, t-butyl, n-pentyl, i-pentyl, s-pentyl, 1,1-dimethylpropyl and neopentyl groups. An alkenyl group may suitably contain 2 to 8 carbon atoms. A cycloalkyl or cycloalkenyl group may have from 3 to 8 carbon atoms, most preferably 3 to 6 carbon atoms, and especially 5 or 6. An acyl group consists of a carbonyl group connected to a hydrogen atom or an optionally substituted alkyl, aryl or heteroaryl group and suitably contains 2 to 8 carbon atoms.

An aryl group may suitably contain from 6 to 10 carbon atoms and is preferably a phenyl or a naphthyl group. A heteroaryl group may be mono- or polycyclic. It suitably comprises 5- and/or 6-membered heterocycles, containing one or more sulphur and/or nitrogen and/or oxygen atoms. Any or all of the constituent groups may be optionally substituted.

When any groups are designated as being optionally substituted, the substituent groups which are optionally present may be any of those customarily employed in the development of pesticidal compounds, and/or the modification of such compounds to influence their structure/activity, persistence, penetration or other property. In relation to moieties defined above as comprising an optionally substituted alkyl, alkenyl or cycloalkyl group, including alkyl parts of aralkyl, heteroaralkyl or acyl groups, specific examples of such substituents include halogen, especially fluorine, chlorine or bromine atoms, and nitro, cyano, hydroxyl, $C_{1-4}$ alkoxy, $C_{1-4}$ haloalkoxy, ($C_{1-4}$ alkoxy)carbonyl groups, phenyl, amino, alkyl- and phenyl-sulphinyl, phenyl-sulphenyl, alkyl- and phenyl-sulphonyl groups, and mono- or di-($C_{1-4}$ alkyl)amino groups. It is preferred, however, that such moieties are unsubstituted, or halogen-substituted.

In relation to moieties defined above as comprising an optionally substituted aryl or heteroaryl group, including acyl groups, optional substituents include halogen, especially fluorine, chlorine and bromine atoms, and nitro, cyano, amino, hydroxyl, $C_{1-4}$ alkyl, $C_{1-4}$ haloalkyl (especially $CF_3$), $C_{1-4}$alkoxy and $C_{1-4}$ haloalkoxy groups. 1 to 5 substituents may suitably be employed.

The compounds are oils, gums, or, predominantly, crystalline solid materials. For example, they can be used in agriculture or related fields for the control of undesired plants. The compounds of general formula I according to the invention possess a high herbicidal activity within a wide concentration range and at low dosages, and may be used in agriculture without any difficulties.

Suitably, at least one of $R^1$ and $R^2$ represents an optionally substituted alkyl, cycloalkyl, alkenyl, cycloalkenyl, phenyl, pyridyl, furyl or thiophenyl group, the other has one of these preferred meanings or represents hydrogen.

Most preferably, $R^2$ represents hydrogen.

Preferably, $R^1$ represents an optionally substituted $C_{1-6}$ alkyl group, $C_{2-6}$ alkenyl group or $C_{3-8}$-cycloalkyl group, in particular a cyclopentyl or cyclohexyl group, or a phenyl or benzyl group which is unsubstituted, or substituted by one or more moieties independently selected from halogen atoms, $C_{1-4}$ alkyl groups, $C_{1-4}$ alkoxy groups and $C_{1-4}$ haloalkyl groups, or a thiophene group which is unsubstituted, or substituted by a halogen atom.

Most preferably, $R^1$ represents a tert-butyl group, an isobutyl group, an isopropyl group, a 2-methoxyethyl group, a cyclopentyl group, a cyclohexyl group, a styryl group, a phenyl or a benzyl group which is unsubstituted, or substituted by one or two moieties selected from fluorine and chlorine atoms, trifluoromethyl groups and methoxy groups, or a thiophene group which is optionally substituted by a chlorine atom.

Preferably, $R^3$ represents a hydrogen atom.

Suitably, Ar represents an optionally substituted aryl or heteroaryl group.

Preferably, Ar represents a phenyl group, which is optionally substituted by 1–2 halogen atoms or a heteroaryl group, which is selected from the group consisting of a furyl, pyridyl, thiophenyl or benzothiophene group, optionally substituted by 1 or 2 moieties selected from halogen and $C_{1-4}$ alkyl.

The thiophenyl group includes the thiophen-2-yl and thiophen-3-yl group.

Preferably, $R^4$ represents a hydrogen atom or a methyl group, in particular a methyl group, and Ar represents an unsubstituted phenyl group or a thiophenyl group which is optionally substituted by one or more halogen atoms.

Included in the scope of the present invention are (R) and (S) isomers of compounds of general formula I having an optical centre and the racemates thereof, and salts, N-oxides and acid addition compounds.

Particularly interesting activity has been found in (S)-isomer compounds of general formula I wherein the group —CH(Ar)$R^4$ is optically active.

The invention is exemplified by the following specific compounds:

(S)-5-tert-butyl-oxazole-2-carboxylic acid (1-thiophen-2-yl-ethyl)-amide, (S)-5-phenyl-oxazole-2-carboxylic acid (1-phenylethyl)-amide, (R/S)-5-phenyl-oxazole-2-carboxylic acid (1-thiophen-2-yl-ethyl)-amide, (S)-5-tert-butyl-oxazole-2-carboxylic acid (1-phenylethyl)-amide, (R/S)-5-tert-butyl-oxazole-2-carboxylic acid (1-thiophen-2-yl-ethyl)-amide, (S)-5-(4-fluorophenyl)-oxazole-2-carboxylic acid (1-phenylethyl)-amide, (R/S)-5-(4-fluorophenyl)-oxazole-2-carboxylic acid (1-thiophen-2-yl-ethyl)-amide, (S)-5-(2,4-difluorophenyl)-oxazole-2-arboxylic acid (1-phenylethyl)-amide, (R/S)-5-(2,4-difluorophenyl)-oxazole-2-carboxylic acid (1-thiphen-2-yl-ethyl)-amide, (R/S)-5-tert-butyl-oxazole-2-carboxylic acid (1-thiophen- 3-yl-ethyl)-amide, (S)-5-tert-butyl-oxazole-2-carboxylic acid (1-thiophen-3-yl-ethyl)-amide, (R/S)-5-phenyl-oxazole-2-carboxylic acid (1-thiophen-3-yl-ethyl)-amide, (S)-5-phenyl-oxazole-2-carboxylic acid (1-thiophen-3-ethyl)-amide, (S)-5-(4-fluorophenyl)-oxazole-2-carboxylic acid (1-thiophen-3-yl-ethyl)-amide, (R/S)-5-phenyl-oxazole-2-carboxylic acid (1-thiophen-2-yl-ethyl)-amide.

The invention also provides a process for the preparation of a compound of general formula I, which comprises reacting a respective compound of the general formula II,

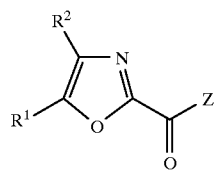

(II)

wherein
$R^1$ and $R^2$ are as defined hereinbefore and
Z represents a leaving group,
with a compound of general formula III,

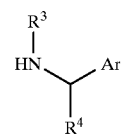

(III)

wherein
$R^3$, $R^4$ and Ar are as defined hereinbefore, or a salt thereof.

A suitable leaving group Z is a halogen atom, especially chlorine; an acyloxy group, for example, acetoxy; an alkoxy group, suitably a methoxy or ethoxy group; or an aryloxy group, for example, a phenoxy group or a hydroxy group. Preferably, Z is a hydroxy, methoxy or ethoxy group.

In practice, the reaction may be carried out in the absence or presence of a solvent which promotes the reaction or at least does not interfere with it, for example toluene, xylene, ethanol, methanol, isopropanol. Mixtures thereof may also be employed.

When Z is an alkoxy group, the reaction is suitably carried out in an organic solvent, for example ethanol or toluene, and within a temperature range from room temperature to the boiling point of the mixture. The reaction has been found to work most effectively when carried out under basic conditions. The basic conditions can suitably be provided by employing an excess of the amine III in the reaction, suitably a twofold excess of III with respect to II. Alternatively, the basic conditions can be provided by the separate inclusion of a base in the reaction mixture with III and II. The base may be any of those commonly employed in organic chemistry, for instance, a hydroxide, hydride, alkoxide, carbonate or hydrogen carbonate salt of a metal from Groups I or II of the Periodic Table; or an amine. A particularly suitable base is a tertiary amine, for example triethylamine.

In a particularly preferred process according to the invention, a compound of formula I is prepared by reacting a compound of formula II in which Z represents hydroxy with the corresponding amine of formula III in the presence of an activating dehydration agent. Such activating dehydration agents are commonly employed in organic chemistry, for instance, dicyclohexylcarbodiimide, carbonyl diimidazole or N-ethoxycarbonyl-2-ethoxy-1,2-dihydroquinoline.

In a variation of the above process, a compound of formula I is prepared by reacting a respective compound of formula II with a salt of general formula IIIa

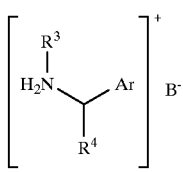

(IIIa)

wherein $R^3$, $R^4$ and Ar are as defined previously and B is a general anionic species, in the presence of a base. The reaction is suitably carried out in an organic solvent, for example ethanol or toluene, and within a temperature range from room temperature to the boiling point of the mixture. The base may be any of those commonly employed in organic chemistry, for instance, a hydroxide, hydride, alkoxide, carbonate or hydrogen carbonate salt of a metal from Groups I or II of the Periodic Table; or an amine. A particularly suitable base is a tertiary amine, for example triethylamine, which may be present in a several-fold excess, for example four-fold.

The starting oxazole-2-carboxylates of formula II can be prepared according to the following reaction scheme using methods which are known to the skilled worker e.g. Chiaki Tanaka Yakagaku Zasshi 85(3) 186–93 (1965) (=CA 58 3407d, 1965):

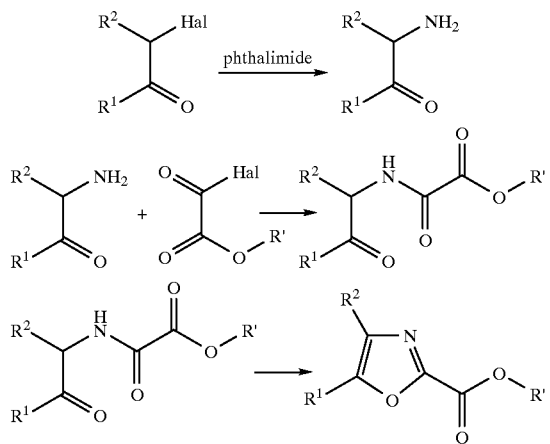

($R^1$ represents hydrogen or alkyl)

The compounds of general formula I have been found to show interesting activity as herbicides. Accordingly, the invention further provides a herbicidal composition comprising a compound of formula I as defined above in association with at least one carrier, and a method of making such a composition which comprises bringing a compound of formula I into association with at least one carrier. Preferably, there are at least two carriers, at least one of which is a surface-active agent.

The invention also provides a method of combating undesired plant growth at a locus, comprising application of such a compound or composition.

Particularly interesting activity has been found against grasses and broad leaf weeds, pre- and post-emergence. Selectivity in important crop species such as wheat, barley, maize, rice and soya-beans has also been found. This activity provides a further aspect of the present invention.

In a method as mentioned above, the dosage of the active ingredient, the compound of general formula I, may, for example, be from 0.01 to 10 kg/ha, suitably 0.05 to 4 kg/ha. The locus may be an agricultural or horticultural locus, comprising, for example, a plant or soil. In a preferred method the locus contains undesired plant growth and treatment is by foliar spray application.

The invention also provides the use of a compound as defined above, as a herbicide. A carrier in a composition according to the invention is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating pesticidal compositions may be used. Preferably, compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus, preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be non-ionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkaryl sulphonates such as dodecylbenzene sulphonate; and polymers of ethylene oxide and copolymers of ethylene oxide and propylene oxide.

The compositions of the new invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10% w of active ingredient. Granules are usually prepared to have a particle size between 10 and 100 BS mesh (1.676–0.152 mm), and may be manufactured by agglomeration or impregnation techniques. Generally, granules will contain 0.5–75% w active ingredient and 0–10% w of additives such as stabilisers, surfactants, slow release modifiers and binding agents. The so-called 'dry flowable powders' consist of relatively small granules having a relatively higher concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The active ingredients according to the invention can be employed alone or as formulations in combination with conventional herbicides. Such combinations of at least two herbicides can be included in the formulation or also added in a suitable form with the preparation of the tank mix. For such mixtures at least one of the following known herbicides can be used:

amethydione, metabenzthiazuron, metamitron, metribuzin, 2,4-D, 2,4-DB, 2,4-DP, alachlor, alloxydim, asulam, atrazine, bensulfuron, bentazon, bifenox, bromoxynil, butachlor, chloridazon, chlorimuron, chlorpropham, chlorsulfuron, chlortoluron, cinmethylin, clopyralid, cyanazine, cycloate, cycloxydim, dichlobenil, diclofop, EPTC, ethiozin, fenoxaprop, fluazifop, fluometuron, fluridone, fluroxypyr, fomesafen, glyphosate, haloxyfop, hexazinone, imazamethabenz, imazapyr, imazaquin, imazethapyr, ioxynil, isoproturon, lactofen, MCPA, MCPP, mefenacet, metazachlor, metolachlor, metsulfuron, molinate, norflurazon, oryzalin, oxyfluorfen, pendimethalin, picloram, pretilachlor, propachlor, pyridate, quizalofop, sethoxydim, simetryn, terbutryn, thiobencarb, triallate, trifluralin, diflufenican, propanil, triclopyr, dicamba, desmedipham, acetochlor, fluoroglycofen, halosafen, tralkoxydim, amidosulfuron, cinosulfuron, nicosulfuron, pyrazosulfuron, thiameturon, thifensulfuron, triasulfuron, tribenuron, esprocarb, prosulfocarb, terbutylazin, benfuresate, clomazone, dimethazone, dithiopyr, isoxaben, quinchlorac, quinmerac, sulfosate.

Mixtures with other active ingredients like fungicides, insecticides, acaricides and nematicides are possible.

The invention is illustrated by the following Examples.

EXAMPLE 1

(S)-5-tert-Butvl-oxazole-2-carboxylic acid (1-thiophen-2-yl-ethyl)-amide (a) 2-(3,3-Dimethyl-2-oxo-butyl)-isoindole-1,3-dione Potassium phthalimide (82.86 g, 0.447 mol) is added to a stirred solution of bromopinacolone (80.10 g, 0.447 mol) in toluene (300 ml). The suspension is refluxed for 19 h, cooled, and then the precipitate is filtered off and discarded. The filtrate is cooled in an ice-bath and treated with petroleum ether (550 ml). The resulting precipitate is collected by filtration. The mother liquor is reduced to circa 100 ml by evaporation in vacuo, and a further quantity of precipitate which forms is collected by filtration and combined with the first crop, giving 2-(3,3-dimethyl-2-oxo-butyl)-isoindole-1,3-dione (total yield 83.5 g, 76%) as colourless crystals, m.p. 96–99° C.

(b) 1-Amino-3,3-dimethyl-butan-2-one

A solution of hydrochloric acid, prepared from concentrated hydrochloric acid (470 ml) and water (235 ml), is added dropwise over 20 min to a stirred solution of 2-(3,3-dimethyl-2-oxo-butyl)-isoindole-1,3-dione (83.5 g, 0.34 mol) in a mixture of glacial acetic acid (330 ml) and water (235 ml). During the addition, the temperature rises from 18° C. to 23° C. The mixture is heated gradually to reflux and then refluxed for 16 h. The solution is cooled and evaporated to dryness in vacuo. The residue is dissolved in water (320 ml) and cooled, and the phthalic acid is filtered off. The filtrate is evaporated in vacuo and the crude product is recrystallised from 2-propanol (180 ml) to give 1-amino-3,3-dimethyl-butan-2-one (37.8 g, 73%) as colourless crystals, m.p. 206–210° C.

(c) N-(3,3-Dimethyl-2-oxo-butyl)-oxalamic acid ethyl ester

Triethylamine (38.5 ml, 0.28 mol) is added to a stirred solution of 1-amino-3,3-dimethyl-butan-2-one (35.0 g, 0.23 mol) in toluene (500 ml). A solution of ethyl oxalyl chloride (31.3 ml, 0.28 mol) in toluene (150 ml) is added dropwise over 15 min, during which time the temperature of the mixture rises from 20° C. to 45° C. The mixture is then refluxed for 2.5 h, and allowed to cool overnight. The reaction mixture is poured into ice-water, stirred vigorously, and the phases are separated. The organic phase is added to sodium hydrogen carbonate solution (500 ml), stirred, and the organic phase is separated, washed twice with water, dried over sodium sulfate and evaporated in vacuo. The residue is triturated with petroleum ether to give N-(3,3-dimethyl-2-oxo-butyl)-oxalamic acid ethyl ester (38.4 g, 78%) as beige crystals, m.p. 82–85° C.

(d) 5-tert-Butyl-oxazole-2-carboxylic acid ethyl ester

Phosphorus oxychloride (16.3 ml, 0.178 mol) is added to a stirred solution of N-(3.3-dimethyl-2-oxo-butyl) oxalamic acid ethyl ester (38.4 g, 0.178 mol) in toluene (p150 ml). The mixture is heated gradually to reflux, and then refluxed for 16 h. After cooling, the mixture is added portionwise to water (500 ml) and stirred vigorously. The organic phase is separated and washed thoroughly with saturated sodium hydrogen carbonate solution (500 ml) and then twice with water (500 ml). The organic phase is then dried over sodium sulfate and evaporated in vacuo. The residue is purified by flash column chromatography (silica gel, petroleum ether/ethyl acetate 7:3 v/v) to give 5-tert-butyl-oxazole-2-carboxylic acid ethyl ester (20.23 g, 58%) as an oil.

(e) 5-tert-Butyl-oxazole-2-carboxylic acid

A solution of sodium hydroxide (0.96 g, 24 mmol) in water (25 ml) is added to a stirred solution of 5-tert-butyl-oxazole .2-carboxylic acid ethyl ester (3.94 g, 20 mmol) In ethanol (35 ml), and the mixture is warmed to 60° C. and stirred for 1 h. The ethanol is then removed by distillation and the aqueous residue is washed with diethyl ether and acidified with 5 N hydrochloric acid. The resulting precipitate is collected by filtration and dried to give 5-tert-butyl-oxazole-2-carboxylic acid (2.30 g, 68%) as beige crystals. This material is used immediately without further purification since, on prolonged storage, it undergoes spontaneous decarboxylation to 5-tert-butyl-oxazole.

(f) (S)-5-tert-Butyl-oxazole-2-carboxylic acid (1-thiophen-2-yl-ethyl)-amide

A solution of carbonyl diimidazole (CDI) (2.42 g, 15 mmol) in THF (40 ml) is added to a stirred solution of 5-tert-butyl-oxazole-2-carboxylic acid (2.3 g, 13.6 mmol) in THF (40 ml). The mixture is stirred for 30 min, then (S)-(1-thiophen-2-yl-ethyl)-amine (2.59 g, 20.4 mmol) is added, followed 10 min later by a solution of DBU (2.24 ml, 15 mmol) in THF (20 ml). The mixture is refluxed for 16 h and the THF is then removed by distillation. The residue is dissolved in ethyl acetate and the organic solution is washed with 2N hydrochloric acid and then twice with water. The organic phase is dried over sodium sulfate and evaporated in vacuo. The residue is purified by flash column chromatography (silica gel, petroleum ether/ethyl acetate 7:3 v/v) to give (S)-5-tert-butyl-oxazole-2-carboxylic acid (1-thiophen-2-yl-ethyl)-amide (2.40 g, 63%) as an oil.

Further Examples are prepared according to the general method of Example 1 and are listed in Table 1. The structures of all products are confirmed by NMR spectroscopy.

TABLE 1

| Ex. No. | R$^1$ | Ar | R$^4$ | Stereo-chem. | M. Pt. (° C.) |
|---|---|---|---|---|---|
| 2 | Phenyl | Phenyl | Me | (S) | 90–93 |
| 3 | Phenyl | 2-Thienyl | Me | (R/S) | 145–148 |
| 4 | t-Butyl | Phenyl | Me | (S) | oil |
| 5 | t-Butyl | 2-Thienyl | Me | (R/S) | oil |
| 6 | 4-Fluoro-Phenyl | Phenyl | Me | (S) | 88–90 |
| 7 | 4-Fluoro-Phenyl | 2-Thienyl | Me | (R/S) | 137–139 |
| 8 | 2,4-di-Fluoro-Phenyl | Phenyl | Me | (S) | 121–123 |
| 9 | 2,4-di-Fluoro-Phenyl | 2-Thienyl | Me | (R/S) | 138–140 |
| 10 | t-Butyl | 3-Thienyl | Me | (R/S) | 53–55 |
| 11 | t-Butyl | 3-Thienyl | Me | (S) | oil |
| 12 | Phenyl | 3-Thienyl | Me | (R/S) | 124–126 |
| 13 | Phenyl | 3-Thienyl | Me | (S) | 88–91 |
| 14 | 4-Fluoro-Phenyl | 3-Thienyl | Me | (S) | 143–145 |
| 15 | Phenyl | 2-Thienyl | Me | (S) | oil |

Herbicidal Activity

To evaluate their herbicidal activity, compounds according to the invention are tested using a representative range of plants:

| | |
|---|---|
| TRZAW | *Triticum aestivum* |
| HORVW | *Hordeum vulgare* |
| ZEAMX | *Zea mays* |
| ORYSA | *Oryza sativa* |
| GLXMA | *Glycine max* |
| ALOMY | *Alopecurus myosuroides* |
| SETVI | *Setaria viridis* |
| ABUTH | *Abutilon theophrasti* |
| AMARE | *Amaranthus retroflexus* |
| AMBEL | *Ambrosia artemisifolia* |
| CHEAL | *Chenopodium album* |
| GALAP | *Galium aparine* |
| IPOHE | *Ipomoea hederacea* |
| MATIN | *Matricaria inodora* |
| STEME | *Stellaria media* |

The tests fall into two categories, pre-emergence and post-emergence. The pre-emergence tests involve spraying a liquid formulation of the compound onto the soil in which the seeds of the plant species mentioned above has recently been sown. The post-emergence tests involve spraying a liquid formulation of the compound onto seedling plants of the above species.

The soil used in the tests is a prepared horticultural loam. The formulations used in the tests are prepared from solutions of the test compounds in acetone containing 0.4% by weight of an alkylphenol/ethylene oxide condensate available under the trade mark TRITON X-155. These acetone solutions are diluted with water and the resulting formulations applied at dosage levels corresponding to 200 g, 400 g, 800 g or 1600 g of active material per hectare in a volume equivalent to 900 liters per hectare.

In the pre-emergence tests untreated sown soil and in the post-emergence tests untreated soil bearing seedling plants are used as controls.

The herbicidal effects of the test compounds are assessed visually twenty days after spraying the foliage and the soil and are recorded on a 0–9 scale. A rating 0 indicates growth as untreated control, a rating 9 indicates death. An increase of 1 unit on the linear scale approximates to a 10% increase in the level of effect.

The results of the pre-emergence tests are set out in Table 2. An asterisk denotes that the specified plant species is not treated in the test.

TABLE 2

| Ex. No. | Dose g/ha | TRZAW | HORVW | ZEAMX | ORYSA | GLXMA | ALOMY | SETVI | ABUTH |
|---|---|---|---|---|---|---|---|---|---|
| 1 | 1600 | 0 | 0 | 1 | 0 | 3 | 7 | 9 | 9 |
|   | 800 | 0 | 0 | 0 | 0 | 2 | 5 | 7 | 6 |
| 2 | 1600 | 0 | 0 | 0 | 0 | 0 | 0 | 0 | 0 |
|   | 800 | 0 | 0 | 0 | 0 | 0 | 0 | 0 | 0 |
| 3 | 1600 | 0 | 0 | 0 | 0 | 0 | 0 | 0 | 0 |
|   | 800 | 0 | 0 | 0 | 0 | 0 | 0 | 0 | 0 |
| 4 | 1600 | * | * | * | * | * | * | * | * |
|   | 800 | 0 | 0 | 0 | 0 | 2 | 0 | 0 | 5 |
| 5 | 1600 | 2 | 1 | 0 | 0 | 2 | 4 | 5 | 9 |
|   | 800 | 1 | 1 | 0 | 0 | 2 | 4 | 4 | 9 |
| 6 | 1600 | 0 | 0 | 0 | 0 | 0 | 0 | 0 | 0 |
|   | 800 | 0 | 0 | 0 | 0 | 0 | 0 | 0 | 0 |
| 7 | 1600 | 0 | 0 | 0 | 0 | 1 | 0 | 0 | 0 |
|   | 800 | 0 | 0 | 0 | 0 | 0 | 0 | 0 | 0 |
| 8 | 1600 | 0 | 0 | 0 | 0 | 1 | 0 | 0 | 3 |
|   | 800 | 0 | 0 | 0 | 0 | 0 | 0 | 0 | 0 |
| 9 | 1600 | 0 | 0 | 0 | 0 | 1 | 0 | 0 | 0 |
|   | 800 | 0 | 0 | 0 | 0 | 0 | 0 | 0 | 0 |
| 10 | 1600 | 0 | 1 | 2 | 1 | 0 | 8 | 8 | 9 |
|   | 800 | 0 | 0 | 0 | 0 | 0 | 4 | 6 | 0 |
| 11 | 1600 | 1 | 2 | 7 | 2 | 4 | 7 | 8 | 9 |
|   | 800 | 0 | 2 | 5 | 0 | 2 | 6 | 8 | 4 |
| 12 | 1600 | 0 | 0 | 0 | 0 | 0 | 0 | 0 | 2 |
|   | 800 | 0 | 0 | 0 | 0 | 0 | 0 | 0 | 0 |
| 13 | 1600 | 0 | 0 | 0 | 0 | 0 | 0 | 3 | 4 |
|   | 800 | 0 | 0 | 0 | 0 | 0 | 0 | 0 | 0 |
| standard[1] | 800 | * | 0 | 0 | * | * | 4 | 2 | 0 |

| Ex. No. | Dose g/ha | AMARE | AMBEL | CHEAL | GALAP | IPOHE | MATIN | STEME |
|---|---|---|---|---|---|---|---|---|
| 1 | 1600 | * | 4 | 7 | 7 | 9 | 9 | 6 |
|   | 800 | * | 1 | * | 1 | 5 | 7 | 2 |
| 2 | 1600 | * | * | 6 | * | 0 | 0 | * |
|   | 800 | * | * | 5 | * | 0 | 0 | * |
| 3 | 1600 | * | * | 5 | * | 0 | 0 | * |
|   | 800 | * | * | 4 | * | 0 | 0 | * |
| 4 | 1600 | * | * | * | * | * | * | * |
|   | 800 | 5 | * | 0 | 0 | 0 | 0 | 0 |
| 5 | 1600 | 8 | * | 8 | 2 | 9 | 9 | 9 |
|   | 800 | 7 | * | 7 | 1 | 3 | 6 | 5 |
| 6 | 1600 | 0 | 0 | 8 | * | 0 | 0 | 0 |
|   | 800 | 0 | 0 | 0 | * | 0 | 0 | 0 |
| 7 | 1600 | 0 | 0 | 8 | * | 0 | 0 | 0 |
|   | 800 | 0 | 0 | 0 | * | 0 | 0 | 0 |
| 8 | 1600 | 8 | 0 | 9 | 0 | 0 | 4 | 4 |
|   | 800 | 4 | 0 | 9 | 0 | 0 | 3 | 1 |
| 9 | 1600 | 6 | 0 | 8 | 0 | 0 | 8 | 3 |
|   | 800 | 0 | 0 | 8 | 0 | 0 | 2 | 2 |
| 10 | 1600 | 9 | 3 | 9 | 9 | 5 | 9 | 7 |
|   | 800 | 9 | 3 | 8 | 9 | 0 | 9 | * |
| 11 | 1600 | 9 | 5 | 7 | 8 | 4 | 5 | 8 |
|   | 800 | 9 | 0 | * | 7 | * | * | 8 |
| 12 | 1600 | 2 | 0 | 5 | 0 | 0 | 0 | 0 |
|   | 800 | * | 0 | * | 0 | * | 0 | 0 |
| 13 | 1600 | 5 | 0 | 7 | 0 | 0 | 0 | 0 |
|   | 800 | 5 | 0 | 5 | 0 | 0 | * | 0 |
| standard[1] | 800 | 5 | * | 0 | 2 | 2 | * | * |

[1]The following compound has been used as a standard:

TABLE 2-continued
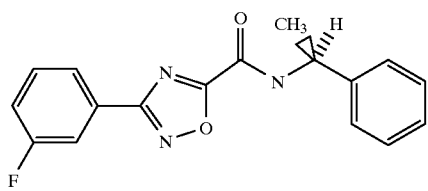
The results of the post-emergence tests are set out in Table 3.
TABLE 3
| Ex. No. | Dose g/ha | TRZAW | HORVW | ZEAMX | ORYSA | GLXMA | ALLOMY | SETVI | ABUTH | AMBEL | AMMRE | CHEAL | GALAP | IPOHE | MATIN | STEME |
|---|---|---|---|---|---|---|---|---|---|---|---|---|---|---|---|---|
| 1 | 800 | 2 | 1 | 1 | 3 | 6 | 4 | 8 | 9 | 9 | 9 | 9 | 5 | 9 | 9 | 9 |
|   | 400 | 1 | 0 | 1 | 2 | 5 | 3 | 8 | 9 | 9 | 9 | 9 | 4 | 7 | 9 | 8 |
|   | 200 | 0 | 0 | 0 | 1 | 3 | 2 | 7 | 9 | 7 | 9 | 9 | 1 | 6 | 9 | 8 |
| 2 | 800 | 2 | 2 | 0 | 2 | 4 | 5 | 6 | 8 | * | * | 9 | 9 | 9 | 4 | * |
|   | 400 | * | * | * | * | * | * | * | * | * | * | * | * | * | * | * |
|   | 200 | * | * | * | * | * | * | * | * | * | * | * | * | * | * | * |
| 3 | 800 | 0 | 2 | 0 | 0 | 2 | 1 | 4 | 2 | * | * | 5 | 4 | 2 | 3 | * |
|   | 400 | 0 | 0 | 0 | 0 | 0 | 0 | 0 | 0 | * | * | 0 | * | 0 | 0 | * |
|   | 200 | 0 | 0 | 0 | 0 | 0 | 0 | * | 0 | * | * | 0 | 0 | 0 | 0 | * |
| 4 | 800 | 2 | 3 | 3 | 4 | 4 | 4 | 5 | 9 | 8 | * | 8 | 5 | 6 | 8 | 6 |
|   | 400 | 0 | 1 | 0 | 3 | 4 | 2 | 4 | 8 | 7 | * | 8 | 4 | 6 | 6 | 5 |
|   | 200 | 0 | 0 | 0 | 0 | 3 | 0 | 0 | 8 | 5 | * | 8 | 1 | 4 | 5 | 4 |
| 5 | 800 | 0 | 1 | 2 | 3 | 5 | 4 | 8 | 9 | 9 | * | 8 | 7 | 9 | 9 | 8 |
|   | 400 | 0 | 0 | 0 | 0 | 3 | 1 | 4 | 9 | 8 | * | 8 | 4 | 9 | 9 | 8 |
|   | 200 | 0 | 0 | 0 | 0 | 2 | 0 | 3 | 7 | 7 | * | 8 | 2 | 5 | 9 | 5 |
| 6 | 800 | 2 | 4 | 2 | 4 | 5 | 5 | 8 | 8 | 9 | 7 | 9 | 8 | 8 | 0 | 9 |
|   | 400 | 1 | 3 | 2 | 2 | 4 | 2 | 7 | 8 | 9 | 4 | 9 | 5 | 8 | 0 | 8 |
|   | 200 | 0 | 2 | 2 | 1 | 4 | 1 | 5 | 5 | 8 | 2 | 8 | 4 | 6 | 0 | 7 |
| 7 | 800 | 2 | 4 | 2 | 2 | 3 | 4 | 7 | 9 | 8 | 2 | 8 | 4 | 6 | 1 | 8 |
|   | 400 | 1 | 2 | 1 | 2 | 2 | 1 | 1 | 5 | 7 | 1 | 3 | 1 | 2 | 0 | 5 |
|   | 200 | 1 | 2 | 1 | 1 | 1 | 1 | 0 | 4 | 5 | 0 | 2 | 0 | 1 | 0 | 4 |
| 8 | 800 | 2 | 4 | 2 | 1 | 3 | 4 | 6 | 6 | 9 | 6 | 9 | 7 | 5 | 5 | 8 |
|   | 400 | 0 | 2 | 0 | 0 | 2 | 2 | 2 | 4 | 9 | 7 | 6 | 3 | 4 | 4 | 5 |
|   | 200 | 0 | 0 | 0 | 0 | 2 | 0 | 2 | 2 | 6 | 0 | 2 | 0 | 3 | 0 | 3 |
| 9 | 800 | 2 | 2 | 0 | 1 | 2 | 1 | 6 | 7 | 8 | 4 | 9 | 3 | 4 | 4 | 6 |
|   | 400 | 1 | 1 | 0 | 0 | 2 | 0 | 3 | 0 | 4 | 0 | 2 | 0 | 3 | 1 | 3 |
|   | 200 | 0 | 0 | 0 | 0 | 1 | 0 | 2 | 0 | 0 | 0 | 0 | 0 | 0 | 0 | 2 |
| 10 | 800 | 3 | 3 | 3 | 2 | 3 | 5 | 6 | 9 | 8 | 5 | 8 | 6 | 6 | 8 | 9 |
|    | 400 | 1 | 1 | 1 | 1 | 1 | 3 | 6 | 9 | 8 | 2 | 7 | 4 | 6 | 7 | 8 |
|    | 200 | 1 | 1 | 1 | 0 | 0 | 2 | 5 | 7 | 7 | 2 | 6 | 4 | 6 | 5 | 5 |
| 11 | 800 | 2 | 1 | 2 | 2 | 6 | 5 | 7 | 9 | 9 | 5 | 8 | 6 | 9 | 8 | 9 |
|    | 400 | 1 | 1 | 2 | 2 | 5 | 4 | 6 | 7 | 9 | 3 | 7 | 4 | 9 | 7 | 9 |
|    | 200 | 0 | 0 | 1 | 1 | 2 | 2 | 5 | * | 9 | 0 | 7 | 4 | 5 | 7 | 7 |
| 12 | 800 | 0 | 2 | 0 | 0 | 3 | 4 | 7 | 9 | 9 | 8 | 8 | 5 | 6 | 7 | 7 |
|    | 400 | 0 | 0 | 0 | 0 | 2 | 0 | 5 | 6 | 9 | 6 | 6 | 0 | 2 | 5 | 7 |
|    | 200 | 0 | 0 | 0 | 0 | 1 | 0 | 2 | 4 | 4 | 3 | 3 | 0 | 1 | 3 | 5 |
| 13 | 800 | 0 | 2 | 0 | 2 | 5 | 6 | 7 | 9 | 9 | 9 | 6 | 9 | 9 | 9 | 8 |
|    | 400 | 0 | 2 | 0 | 2 | 4 | 4 | 6 | 9 | 9 | 9 | 6 | 5 | 9 | 8 | 7 |
|    | 200 | 0 | 0 | 0 | 1 | 4 | 0 | 3 | 9 | 9 | 9 | 6 | 5 | 4 | 6 | 7 |
| standard[1] | 800 | 1 | 3 | 3 | * | * | 4 | 6 | 6 | 2 | * | 4 | 5 | 5 | * | * |
|    | 400 | 1 | 3 | 1 | * | * | 2 | 6 | 5 | 1 | * | 3 | 4 | 4 | * | * |
|    | 200 | 0 | 2 | 1 | * | * | 0 | 5 | 3 | 0 | * | 2 | 4 | 1 | * | * |
[1]The same compound has been used as standard as was used in the pre-emergence tests of Table 2.

What is claimed is:

1. A compound of the general formula I

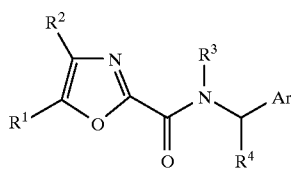

wherein
- $R^1$ and $R^2$ each independently represent a hydrogen atom or an optionally substituted alkyl, alkenyl, $C_{3-8}$ cycloalkyl, $C_{3-8}$ cycloalkenyl, aryl, heteroaryl, with the proviso that the heteroaryl is not 4,5-dihydro-2-oxazolyl group, or benzyl group;
- $R^3$ represents a hydrogen atom, or an alkyl or acyl group;
- $R^4$ represents a hydrogen atom or an alkyl group; and
- Ar represents an optionally substituted aryl or heteroaryl group.

2. A compound as claimed in claim 1, wherein at least one of $R^1$ and $R^2$ represent an optionally substituted alkyl, cycloalkyl, alkenyl, cycloalkenyl, phenyl, pyridyl, furyl or thiophenyl group.

3. A compound as claimed in claim 1, wherein one of the radicals $R^1$ and $R^2$ represents an optionally substituted $C_{1-6}$ alkyl group, $C_{2-6}$ alkenyl group or $C_{2-8}$ cycloalkenyl group, or a phenyl or a benzyl group which is unsubstituted, or substituted by one or more moieties independently selected from halogen atoms, $C_{1-4}$ alkyl groups, $C_{1-4}$ alkoxy groups and $C_{1-4}$ haloalkyl groups, or a thiophene group which is unsubstituted, or substituted by a halogen atom, and the other radical $R^1$ or $R^2$ represents hydrogen.

4. A compound as claimed in claim 2 or 3, wherein
- $R^1$ represents a tert-butyl group, an isobutyl group, an isopropyl group, a 2-methoxyethyl group, a cyclopentyl group, a cyclohexyl group, a styryl group, a phenyl or a benzyl group which is unsubstituted, or substituted by one or two moieties selected from fluorine and chlorine atoms, trifluoromethyl groups and methoxy groups, or a thiophene group which is optionally substituted by a chlorine atom.

5. A compound as claimed in claim 4, wherein
- $R^1$ represents an optionally substituted phenyl group or a tert-butyl group, and
- $R^2$ represents hydrogen.

6. A compound as claimed in claim 1, wherein
- $R^4$ represents a hydrogen atom or an optionally substituted $C_{1-2}$ alkyl group, and
- Ar represents an optionally substituted phenyl group, or an optionally substituted pyridyl, furyl, thiophenyl or benzothiophene group.

7. A compound as claimed in claim 6, wherein
- $R^4$ represents a hydrogen atom or a methyl group and Ar represents an unsubstituted phenyl group or a thiophenyl group which is optionally substituted by a methyl group.

8. A compound as claimed in claim 1, wherein
- the group —CH(Ar)$R^4$ portion of the structure of formula I is optically active and has the (S)-configuration.

9. A compound according to claim 1 selected from the group consisting of:
(S)-5-phenyl-oxazole-2-carboxylic acid (1-thiophen-3-yl-ethyl)-amide, (S)-5-phenyl-oxazole-2-carboxylic acid (1-phenylethyl)-amide, (R/S)-5-phenyl-oxazole-2-carboxylic acid (1-thiophen-2-yl-ethyl)-amide, (S)-5-tert-butyl-oxazole-2-carboxylic acid (1-phenylethyl)-amide, (R/S)-5-tert-butyl-oxazole-2-carboxylic acid (1-thiophen-2-yl-ethyl)-amide, (S)-5-(4-fluorophenyl)-oxazole-2-carboxylic acid (1-phenylethyl)-amide, (R/S)-5-(4-fluorophenyl)-oxazole-2-carboxylic acid (1-thiophen-2-yl-ethyl)-amide, (S)-5-(2,4-difluorophenyl)-oxazole-2-carboxylic acid (1-phenylethyl)-amide, (R/S)-5-(2,4-difluorophenyl)-oxazole-2-carboxylic acid (1-thiophen-2-yl-ethyl)-amide, (R/S)-5-tert-butyl-oxazole-2-carboxylic acid (1-thiophen-3-yl-ethyl)-amide, (S)-5-tert-butyl-oxazole-2-carboxylic acid (1-thiophen-3-yl-ethyl)-amide, (R/S)-5-phenyl-oxazole-2-carboxylic acid (1-thiophen-3-yl-ethyl)-amide, (S)-5-phenyl-oxazole-2-carboxylic acid (1-thiophen-3-yl-ethyl)-amide, (S)-5-(4-fluorophenyl)-oxazole-2-carboxylic acid (1-thiophen-3-yl-ethyl)-amide, (R/S)-5-phenyl-oxazole-2-carboxylic acid (1-thiophen-2-yl-ethyl)-amide.

10. A process for the preparation of a compound of general formula 1, which comprises reacting a respective compound of the general formula II,

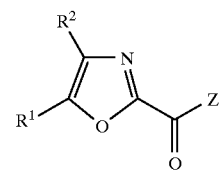

wherein
- $R^1$ and $R^2$ are as defined in claim 1 and
- Z represents a leaving group,
with a compound of general formula III,

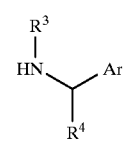

wherein
- $R^3$, $R^4$ and Ar are as defined in claim 1 or a salt thereof.

11. A herbicidal composition comprising at least one compound of general formula I, as claimed in claim 1, together with at least one carrier.

12. A composition as claimed in claim 11, comprising at least two carriers, at least one of which is a surface-active agent.

13. A method of combating undesired plant growth at a locus, comprising application to the locus of a compound of general formula I, as claimed in claim 1.

14. A method of using a compound of general formula I as claimed in claim 1 as a herbicide.

* * * * *